United States Patent [19] [11] Patent Number: 5,019,062
Ryan et al. [45] Date of Patent: May 28, 1991

[54] BICOMPONENT MATERIAL

[75] Inventors: Leslie D. Ryan, Millville; Mark J. Steinhardt, Loveland; Milton D. Spahni, Okeana; James C. Baird, Cincinnati, all of Ohio

[73] Assignee: The Procter & Gamble Company, Cincinnati, Ohio

[21] Appl. No.: 210,672

[22] Filed: Jun. 23, 1988

[51] Int. Cl.⁵ ............................................. A61F 13/15
[52] U.S. Cl. ................................. 604/359; 604/383; 428/323; 428/137
[58] Field of Search .................... 604/383, 359, 360; 428/323, 137

[56] References Cited

U.S. PATENT DOCUMENTS

| 2,418,907 | 4/1947 | Schreiber | 128/284 |
|---|---|---|---|
| 2,542,909 | 2/1951 | De Wet | 167/84 |
| 2,690,415 | 9/1954 | Shuler | 167/84 |
| 3,340,875 | 9/1967 | Dudley et al. | 128/290 |
| 3,416,523 | 12/1968 | Yeremian | 604/383 |
| 3,585,998 | 6/1971 | Hayford et al. | 128/284 |
| 3,691,271 | 9/1972 | Charle et al. | 604/359 |
| 3,732,867 | 5/1973 | Money | 604/359 |
| 3,843,478 | 10/1974 | Zuscik | 161/164 |
| 3,875,942 | 4/1975 | Roberts et al. | 128/287 |
| 3,929,135 | 12/1975 | Thompson | 604/383 |
| 3,939,838 | 2/1976 | Fujinami et al. | 128/290 R |
| 3,968,798 | 7/1976 | Hokanson | 128/284 |
| 4,022,210 | 5/1977 | Glassman | 604/359 |
| 4,055,184 | 10/1977 | Karami | 128/287 |
| 4,059,114 | 11/1977 | Richards | 604/359 |
| 4,321,924 | 3/1982 | Ahr | 128/287 |
| 4,324,246 | 4/1982 | Mullane et al. | 128/287 |
| 4,342,314 | 8/1982 | Radel et al. | 128/287 |
| 4,392,862 | 7/1983 | Marsan et al. | 604/366 |
| 4,521,437 | 6/1985 | Storms | 426/130 |
| 4,525,410 | 6/1985 | Hagiwara et al. | 604/360 |
| 4,547,195 | 10/1985 | Jackson | 604/359 |
| 4,624,666 | 11/1986 | De Rossett et al. | 604/366 |
| 4,663,219 | 5/1987 | Janocha et al. | 428/213 |
| 4,673,402 | 6/1987 | Weisman et al. | 604/368 |
| 4,678,571 | 7/1987 | Hosaka et al. | 210/266 |
| 4,687,478 | 8/1987 | Van Tilburg | 604/387 |
| 4,690,679 | 9/1987 | Mattingly et al. | 604/383 |
| 4,710,186 | 12/1987 | De Rossett et al. | 604/383 |
| 4,713,068 | 12/1987 | Wang et al. | 604/378 |
| 4,725,481 | 2/1988 | Ostapchenko | 428/213 |
| 4,798,604 | 1/1989 | Carter | 604/383 |
| 4,826,497 | 5/1989 | Marcus et al. | 604/359 |
| 4,843,739 | 7/1989 | von Blucher et al. | 36/44 |

Primary Examiner—C. Fred Rosenbaum
Assistant Examiner—Mark O. Polutta
Attorney, Agent, or Firm—E. Kelly Linman; John V. Gorman; Richard C. Witte

[57] ABSTRACT

A bicomponent material which allows liquids to pass in a first direction, but substantially prevents the liquids from passing in the opposite direction, is disclosed. The material also exposes any gases attempting to pass in the direction opposite to that of the liquid transmission to an odor control lamina. The material is especially suitable for use with articles which deal with bodily fluids and the gases generated therefrom.

38 Claims, 3 Drawing Sheets

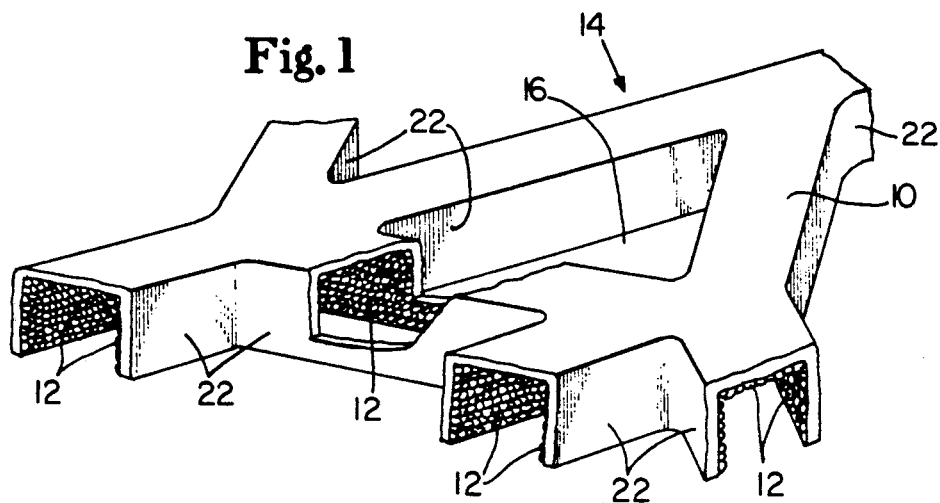
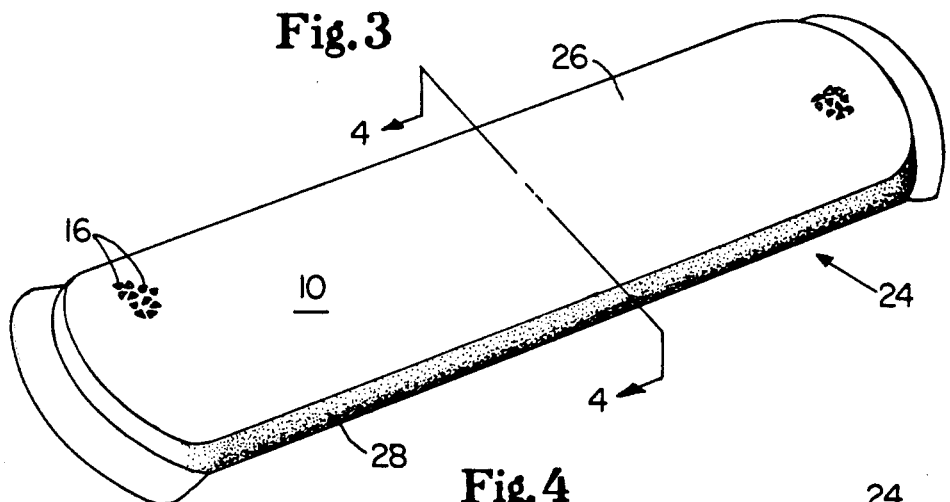
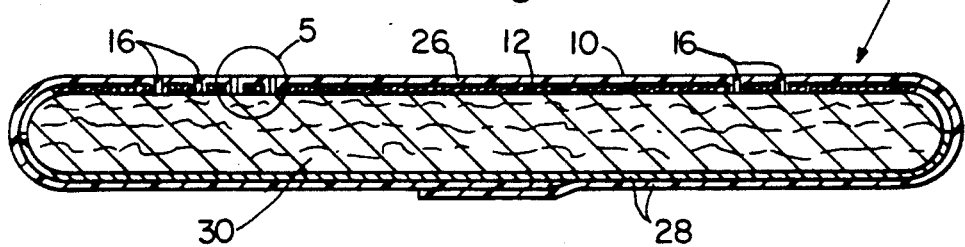
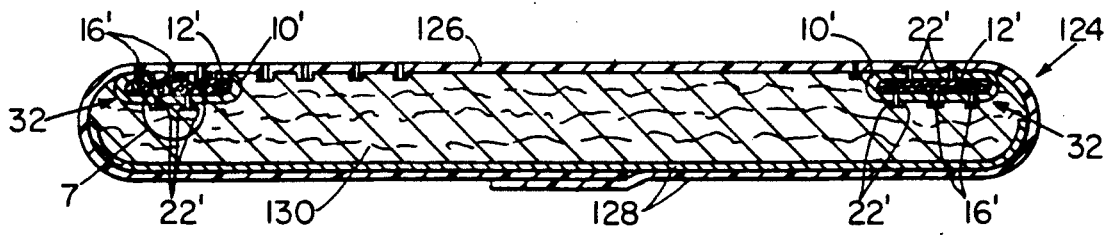

5,019,062

BICOMPONENT MATERIAL

FIELD OF THE INVENTION

This invention relates to films which are exposed to both liquid and gas media, and more particularly to polymeric films through which liquids are transmitted and further provide for odor control.

BACKGROUND OF THE INVENTION

It is often desirable to control, or prevent, the exposure of both liquid and gas media to people. For example, if the liquid is urine or menses, it is desirable to keep the liquid from contacting the skin of the person. Furthermore, it is recognized such liquids often generate malodorous gases which are objectionable.

The prior art has attempted to deal with this problem by absorbing the liquids and/or deodorizing any resultant gases. For example, U.S. Pat. No. 2,690,415, issued to Shuler Sept. 28, 1954, discloses an odor adsorbent medium wherein the active is layered in two strata, one on each side of a core of cushion plies. This assembly, which is then sandwiched by an outer covering, provides no means to control, or contain, any liquids which may generate the gases adsorbed by the active strata.

U.S. Pat. No. 3,939,838, issued to Fujinami et al. on Feb. 24, 1976, discloses a catamenial pad which has a deodorant active dispersed throughout an absorbent core. U.S. Pat. No. 2,418,907, issued to Schreiber on Apr. 15, 1947, discloses a sanitary napkin with a deodorant medium disposed in discrete pockets between the topsheet and absorbent core of the napkin. These teachings, however, suffer from the drawback that malodorous gases exiting the absorbent core towards the topsheet may not encounter the active dispersed therethroughout if such gases are generated at an elevation above the deodorant active, or may encounter the border areas between individual pockets of the deodorant. Furthermore, no means to prevent wetting of the deodorant upon fluid entry, and possibly subsequent loss of efficacy, is provided by these teachings.

BRIEF SUMMARY OF THE INVENTION

It is an object of this invention to provide a material which overcomes the aforementioned problems. Specifically, it is an object of this invention to provide a material which will provide a means for the control of both gases and liquids. More specifically, it is an object of this invention to provide a material which will transmit liquids, and expose any malodors generated by such liquids, or otherwise occurring, to a means of odor control.

The invention comprises a bicomponent film laminate which transmits liquids deposited on the laminate in one direction and exposes an active to malodors attempting to pass through the laminate in the opposite direction. The laminate comprises a first polymeric lamina exhibiting a pattern of discrete apertures and having opposed outwardly and inwardly oriented faces. The outwardly oriented face of the first polymeric lamina is hereinafter interchangeably referred to as the exterior face of the first polymeric lamina, while the inwardly oriented face of the first polymeric lamina is hereinafter interchangeably referred to as the interior face of the first polymeric lamina. The invention also comprises a second lamina having an odor control means and an inwardly oriented or first face adjacent the inwardly oriented or first face of the first lamina and an outwardly oriented or second face opposed thereto. The second lamina has a pattern of discrete apertures, substantially coinciding with the apertures of the first lamina. The laminate permits liquids deposited on the outwardly oriented face of the first lamina to pass through the discrete apertures without substantially wetting the second lamina. It also prevents malodors from passing through the laminate in the direction opposite to the direction of liquid transmission without substantial exposure of the gaseous malodors to the outwardly oriented or second face of the second lamina.

BRIEF DESCRIPTION OF THE DRAWINGS

While the Specification concludes with claims particularly pointing out and distinctly claiming the invention, it is believed that the same will be better understood from the figures taken in conjunction with the following descriptions, wherein like parts are given the same reference number in the figures and similar or analogous parts are designated with a prime symbol or by adding 100 to the prior reference numeral.

FIG. 1 is a cross sectional view of an embodiment of the laminate of the present invention having a formed film first lamina;

FIG. 3 is a perspective view of a catamenial pad incorporating the laminate of FIG. 1 of the present invention;

FIG. 4 is a cross-sectional view of the catamenial pad of FIG. 3, taken along section line 4—4 of FIG. 3;

FIG. 6 is a cross-sectional view of a second embodiment of catamenial pad of the type generally shown in FIG. 3, taken at a point corresponding to section line 4—4 of FIG. 3.

DETAILED DESCRIPTION OF THE INVENTION

Figure 2:
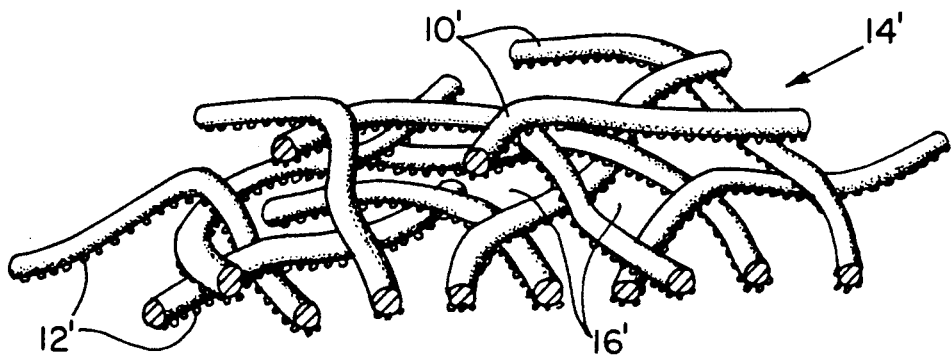
FIG. 2 is a cross sectional view of a second embodiment of the present invention having a nonwoven material first lamina.

The invention comprises a bicomponent material adapted to pass fluids in a first direction and simultaneously inhibit or, substantially prevent, the transmission of gaseous malodors in the opposite direction. The gaseous malodors may, but do not necessarily, emanate from the fluids. The invention is particularly well suited for fluids, or liquids, which may originate from the human body including, for example, menses, other vaginal discharges, blood, urine, and perspiration. Such liquids typically exude malodors which are generally classified as amines, mercaptans, fatty acids and the like. As described below, this invention may be advantageously incorporated into articles of manufacture which deal with bodily liquids, including, but not limited to, catamenial pads, panty liners, bandages, diapers, tissues, bedding, adult incontinent products, underarm shields, foot pads and colostomy aids.

The bicomponent material comprises at least two laminae joined to form a unitary laminate. Obviously both laminae must be provided with a cooperating means to permit liquids to pass through the laminae, otherwise the liquids may become trapped between the laminae and possibly result in delamination. Conversely, both laminae should cooperate to prevent malodors from passing through the laminate in the direction opposite that of fluid transmission.

Referring to FIG. 1, a first polymeric lamina 10 particularly well suited to these ends and which provides a substrate to which the second lamina 12 is applied is a film, such as a polyolefinic thermoplastic, having a thickness ranging from about 0.01 mm to about 0.3 mm (0.0005 to 0.01 inches). An apertured formed film 10 is desirable due to its inherent tendency to be liquid pervious, yet nonabsorbent. Thus, the surface of the formed film 10 will remain dry and hence more comfortable to the wearer should the invention be utilized as a topsheet in one of the exemplary articles of manufacture noted above. It is also important that the first lamina 10, if utilized as the topsheet of an absorbent article, be compliant, soft-feeling and nonirritating to the skin. Other nonlimiting examples of first laminae 10 include woven and nonwoven materials made of polyester, polypropylene, nylon, polyethylene, rayon, and blends thereof.

Optionally, the outer face of the first lamina 10 may be treated with a surfactant to render this surface more hydrophilic, and thereby result in faster penetration of liquids deposited on the surface through the laminate 14. Surfactants sold by Imperial Chemical Industries of London England under the names Atmer 645 and Atmer 685 are suitable. Such a treatment may diminish the likelihood that bodily fluids will flow off of the first lamina 10, or topsheet, and stain clothing. Furthermore, any liquids which are not transmitted through the laminate 14 may emit malodors which are not acted on by the second lamina 12 of the invention.

The second lamina 12 provides the principal means for controlling odors associated either with liquids passing through the laminate 14 or originating from other sources. Known means for odor control include adsorption, absorption, and chemical reaction such as chemical neutralization, including complexation, ion-pairing and the like, or chemically breaking down malodorous gases into constituents which are more readily adsorbed or neutralized. Usually such means act to reduce the liquid vapor pressure of the absorbed fluids and the concentrations of malodorous gases near the second lamina 12.

A preferred adsorbtive material for the second lamina 12 is activated charcoal, such as coconut charcoal, having an average particle size of 2–4 microns. An important advantage of an activated charcoal second lamina 12 is that it imparts increased opacity to the laminate 14, causing transmitted liquids to be somewhat hidden from view by preventing light from being transmitted through the laminate 14 and illuminating liquids which have been transmitted through the laminate 14.

Additionally, from about 1 to about 15 weight percent whiteners may be added to the first lamina 10 to further increase opacity and mask the dark coloring of the charcoal, or other active. Whiteners such as titanium dioxide and calcium carbonate are feasible, and are generally limited by the increased tearability and decreased comfort to the skin of the wearer such whiteners impart to the first lamina 10.

Other adsorbtive materials which work to control odors and may be utilized independently of or in conjunction with the activated charcoal second lamina 12 described above include but are not limited to zeolites or molecular sieve products such as sold by the Union Carbide Company of Danbury, Conn. under the name Abscents, and metal salts of copper, iron, zinc, cobalt and others. An absorbent, such as a polyacrylate absorbent gelling material, may also be used for the second lamina 12.

The second lamina 12 may be joined to the first lamina 10 by mechanical entrapment, adhesion or a combination of both. Adhesive bonding of the laminae provides the advantage that a wide range of materials and forms of materials may be joined by this method.

If adhesive bonding is the selected means to join the two laminae, the adhesive is preferentially applied to the first lamina 10. The adhesive may be applied to the first lamina 10 by spraying from a spray gun having an atomizing nozzle or printing the lamina 10 with the adhesive using a roll coating technique, as is known in the art.

Any means which provides a generally thin, even coating of adhesive, typically about 3.1 to about 3.7 mg. per sq. cm. of substrate, is suitable. It is important that the adhesive, or other joining means, not totally encapsulate or obscure the materials of the second lamina 12, and thereby prevent the second lamina 12 from acting on gaseous malodors. The adhesive is preferably pressure sensitive and safe for epidermal and other human application. Adhesives such as the type sold by Dow Corning of Midland, Mich. under the name 355D Silicone and by Eastman Chemical Products, subsidiary of Eastman Kodak, Rochester, N.Y., under the name Eastobond A-3 have been found to work well.

After the first lamina 10 is coated with adhesive, the material of the second lamina 12, which is typically in a powdered or granular state, is applied to the adhesive. The material comprising the second lamina 12 may be applied by such means as brushing, blowing or spraying against the first lamina 10, drawing the first lamina 10 through a fluidized bed of the second lamina 10 or any means of application known in the art which brings the material of the second lamina 12 into contact with the adhesive of the first lamina 10. A second lamina 12 comprised of a coating of approximately 2.2 to approximately 8.8, typically 5.5 mg., of activated charcoal per sq. cm. has been found to work well.

If desired, the second lamina 12 could be applied to first lamina 10 as a grid, or network of discrete odor control elements (not shown). This is accomplished by applying the adhesive to first lamina 10 in a desired pattern, such that second lamina 12 adheres to first lamina 10 only at specific discrete sites. This arrangement provides the advantage that less of the material comprising second lamina 12 may be used, and substantially full coverage of laminate 14 is maintained. If desired, the density of second lamina 12 can be varied throughout the laminate 14.

Alternatively, the laminae may be joined by mechanical entrapment of the materials comprising the second laminae 12. The first lamina 10 is heated to its melting range, then the second lamina materials 12 are applied, as described above, to the first lamina 10 as it passes between pressure rolls, embedding the materials of second lamina 12 into the first lamina 10. Upon solidification, the materials comprising second lamina 12 materials are entrapped, or embedded, in the first lamina 10. If desired, the first lamina 10 may be adhesive coated prior to passing between the pressure rolls for further assurance the laminae will be joined into a unitary laminate.

After joining, each lamina has an inwardly oriented face associated with an inwardly oriented face of the other lamina and an outwardly oriented face opposed to the outwardly oriented face of the other lamina. The laminae are preferentially contiguously joined and, depending on the material selected for the first lamina, may be apertured or unapertured.

If the laminate 14 is to be used, for example, in a diaper or catamenial pad, the outwardly oriented face of the first, or polymeric film, lamina 10 is oriented towards the body of the wearer and the inwardly oriented face of the first lamina 10 is oriented towards the core of the diaper or pad. The outwardly oriented face of the second, or deodorizing, lamina 12 is oriented towards the core of the catamenial pad or diaper and the inwardly oriented face of the second lamina 12 is oriented towards the body of the wearer.

To permit transmission through the laminate 14 of any liquids deposited on the outwardly oriented face of the first lamina 10, the laminate 14 must be provided with a pattern of discrete apertures 16. If a formed film, as shown in FIG. 1, is used for the first lamina 10, the apertures 16 are preferably provided after the laminae are joined into a unitary laminate 14, as described above, so that the apertures 16 of the laminae are in register, i.e. the apertures 16 of the second lamina 12 substantially coincide with the apertures 16 of the first lamina 10.

Several processes are known and suitable for producing apertures 16 in a formed film laminated structure 14. One such process is to bring the outwardly oriented face of the second lamina 12 into contact with a forming screen which has the desired aperture size and pattern. A vacuum draws the laminate 14 against the forming screen. While the vacuum is applied, a water jet heated to slightly below the melting point of first lamina 10 is passed over the outwardly oriented face of the first lamina 10, perforating and forming the laminate 14 in a configuration corresponding with that of the forming screen.

Circumscribing each perforation, or aperture 16, of the formed film 10 is material, known as cones 22, extruded into the screen and which remains generally perpendicular to the plane of the laminate 14. The cones 22 should have a caliper, defined as the dimension of the cone 22 perpendicular to the plane of the laminate 14, of approximately 0.5 mm (0.02 inches). The cones 22 provide vertical stanchions which prevent liquids deposited on the exterior face of the first lamina 10 and transmitted through laminate 14 from passing back through the laminate 14 from the second lamina 12 towards the first lamina 10. The cones 22, or stanchions, also buffer, or keep, the second lamina 12 away from any liquids transmitted through the laminate 14.

If a woven or nonwoven material is used for the first lamina 10', as shown in FIG. 2, the three-dimensional character of the lamina 10' having fibers of about 0.5 to about 6, typically 3, denier will prevent wetting of all but the exteriorly positioned fibers, and keep any inwardly disposed fibers, and the second laminae 12' associated therewith, from being substantially wetted by transmitted liquids. Several means are potentially available to further prevent wetting of the second lamina 12' associated with a woven or nonwoven fibrous first lamina 10'. For example, the fibers of the first lamina 10' which are disposed opposite the outwardly oriented face of the first lamina 10' could be made of an absorbent material, while the fibers of the first lamina 10' disposed near the outwardly oriented face of the first lamina 10' could be made nonabsorbent. Alternatively, a laminate 14' of the invention could be provided, as described above, having an additional first lamina 10' (not shown) substantially adhered to the side of the laminate 14' having second lamina 12'. This provides a thin, sacrificial layer of the first lamina 10' fibers, not having material of the second lamina 12' associated therewith, continuously joined to the second lamina 12' by means of adhesive. The thin sacrificial layer of the first lamina 10' encounters any liquids transmitted through the laminate 14', and provides a standoff distance between such liquids and the second lamina 12', thereby keeping the second lamina 12' substantially dry.

Adhesive may be applied to a woven or nonwoven material 10', or any other apertured first lamina 10', as illustrated in FIG. 2, by roll printing. The roll pressure must be adjusted to prevent obturating the apertures 16' with the adhesive. Another means to provide adhesive to woven and nonwoven materials is to coextrude the adhesive with the fibers of the materials, using known techniques, so that approximately one-half of the fiber cross-section is composed of adhesive, following which the fibers are formed into a woven or nonwoven lamina 10' using conventional techniques. After forming the fibers into first laminate 10', the material of the second lamina 12' is applied using any of the aforementioned techniques.

A third means (not shown) to substantially prevent wetting of the second lamina 12 of any laminate 14 described herein is to provide a material having high hydrophilicity, such as an absorbent gelling material, typically a polyacrylate, in the vicinity of the outwardly oriented face of the second lamina 12'. This will remove any deposited fluids which pass through the laminate 14, thereby diminishing exposure of such liquids to the second lamina 12 and preventing the liquids from migrating towards the outwardly oriented face of the second lamina 12 after passing through the laminate 14. A polyacrylate of the type disclosed by U.S. Pat. No. 4,654,039 issued to Brandt et al., and which is incorporated herein by reference, is suitable. Such materials often swell, or expand, in the presence of water, therefore care must be taken to associate the polyacrylate with laminate 14 in a position where the polyacrylate can expand without coming into substantial contact with the laminate 14, and particularly second lamina 12.

It may be further possible to incorporate the material of the second lamina into a basis matrix of the first lamina (not shown). For example, an open cell foam sheet can be provided with a density which increases throughout the thickness of the foam sheet. This causes any liquids deposited on the top, or less dense areas, of the foam to be rapidly transmitted via an internal capillary network to the more dense underlying foam areas. The density gradient will prevent any such transmitted liquids from returning to the top surface of the foam, entrapping such liquids in the underlying areas. If desired, absorbent gelling materials, such as polyacrylate, may be provided in the underlying areas of the foam to further ensure rapid transmission of deposited liquids through the upper parts of the foam and prevent the return of such liquids to the top of the foam sheet.

Dispersed throughout the foam sheet, and above the elevation of any absorbent gelling materials, is the second lamina. This second layer is provided during the manufacture of the foam by adding the granular materials before the foam solidifies. The second lamina is preferably positioned at a high elevation within the foam matrix, so that any liquids will be rapidly transmitted past the elevation of the second lamina, keeping the second lamina from being substantially wetted by the liquids. The second lamina must also be above the elevation of any liquids collected in the lower elevation of the foam to prevent wetting from absorbed liquids, as well as liquids being transmitted to the lower elevation. However, malodors emanating from the transmitted liquids, or other sources, will encounter the second lamina as such malodors migrate towards the top of the foam.

A laminate 14 having approximately 5 to approximately 60 percent, open area, typically about 25 percent, is generally sufficient to transmit deposited liquids, while preventing malodor transmission without substantial exposure of the malodors to the second active lamina 12. The percent open area of a fibrous laminate 14' may be varied according to the density and distribution of fibers, while the percent open area of a formed film laminate 14 may be varied by adjusting the size and spacing of the apertures 16.

If the invention is to be used in conjunction with liquids or gases which originate from the human body, it may be desirable to associate the laminate 14 with a means for collecting liquids which pass through said laminate and/or a means for collecting gases which are prevented from passing in the opposite direction through said laminate without substantial exposure to odor control lamina 12. Several such means will be apparent to one skilled in the art and nonlimiting examples wherein the laminate 14 is executed in a catamenial pad, and relatedly in a diaper or adult incontinent product, having both means to collect transmitted liquids and nontransmitted gases is provided below. A further example of incorporating the laminate 4 of this invention into bedding is provided.

Referring to FIG. 3, a catamenial pad 24 comprises a liquid permeable topsheet 26, a liquid impermeable backsheet 28 and an absorbent core means 30 disposed therebetween. As shown in FIG. 4, the absorbent core means 30 has a first face and a second face opposed thereto. The backsheet 28 overlays the first face of the core means 30, sealing the sides, ends and bottom of the pad 24 and contacts the undergarment of the wearer when the catamenial pad 24 is in use. The topsheet 26 overlays the second face of the core means 30 and is placed against the body of the wearer when the catamenial pad 24 is in use.

Figure 5:
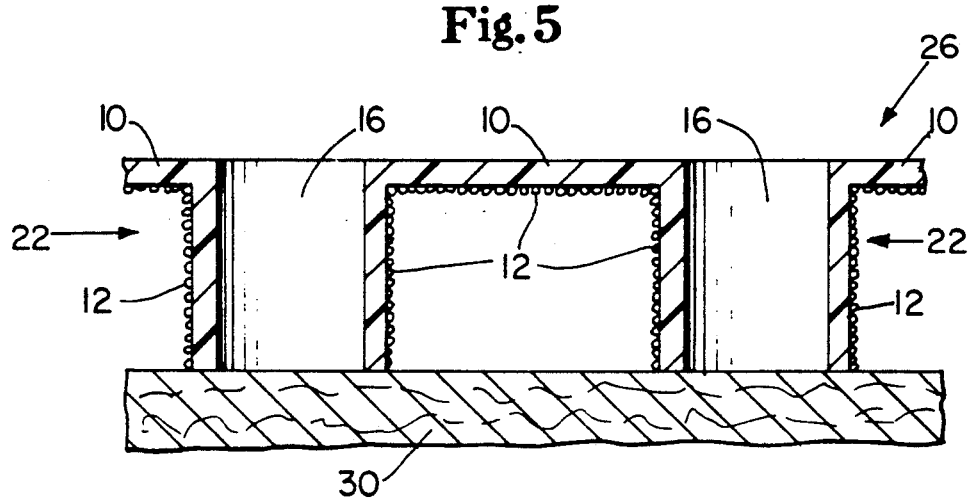
FIG. 5 is an enlarged view of the topsheet of the catamenial pad of FIG. 4.
Figure 7:
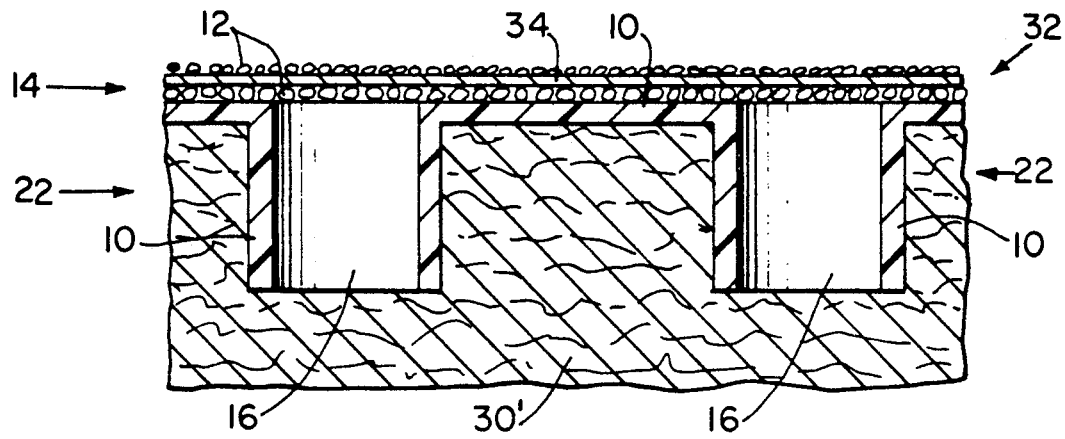
FIG. 7 is an enlarged cross-sectional view of one of the tubes of the catamenial pad of FIG. 6.

As shown in FIG. 5, the topsheet 26 of the pad may be composed of the bicomponent formed film laminate 14 described above, and illustrated by FIG. 1, the details of which will not be repeated here. Topsheets 26 having a first lamina 10 constructed according to the teachings of U.S. Pat. No. 4,342,314 issued to Radel et al. and U.S. Pat. No. 3,929,135 issued to Thompson work well. It is to be recognized that a woven or nonwoven laminate 14, as illustrated by FIG. 2, topsheet 26 could be used in place of the formed film topsheet 26. The outwardly oriented face of the first lamina 10 is oriented towards the body of the wearer while the outwardly oriented face of the second lamina 12 is oriented towards the core means 30. It is important that the materials of the first and second laminae provide a topsheet 26 which exhibits good strikethrough and rewet characteristics, permitting liquids, such as menses or other vaginal discharges, to rapidly penetrate the topsheet 26 and preventing such liquids from flowing back through the topsheet 26. These characteristics will present a pad 24 which not only is clean in appearance, but also does not soil clothing or bedding in the vicinity of the pad 24. A catamenial pad 24 having a topsheet 26 of approximately 90 sq. cm., a first lamina 10 of low density polyethylene and a second lamina 12 comprising about 200 to about 800 mg., preferably about 500 mg., activated charcoal has been discharge of about 40 ml and provide for extended wear periods.

The absorbent core means 30 provides the means to collect liquids deposited on the outwardly oriented face of the first lamina 10, i.e. the top of the catamenial pad 24. The core means 0 should be conformable and nonirritating to the skin. Suitable materials include layers of tissue, such as cellulose wadding, and fibrated comminution pulp, or airfelt. The core means 30 need not have a total absorbent capacity much greater than the total amount of menstrual fluid to be absorbed, and is preferably narrow and thin so as to be comfortable to the wearer. Generally about 6 grams comminuted wood pulp absorbs a heavy menstrual discharge of about 40 ml.

The backsheet 28 may be any flexible, liquid impervious film, preferably low density polyethylene, and prevents liquids absorbed by the core means 30 from soiling the clothing of the wearer. The backsheet 28 should also be impervious to malodorous gases generated by the absorbed liquids so that such malodors do not escape and become noticed by the wearer. A low density polyethylene backsheet 28 of about 0.01 to about 0.05 mm (0.0005 to 0.002 inches) in thickness has been found to work well.

To assemble the pad, the inner surface of the backsheet 28 and the outwardly oriented face of the second lamina 12 are placed in register with opposed sides of the core means 30. The topsheet 26 and backsheet 28 are then wrapped around the core means 30 and secured together along a gas and fluid tight seam, which is formed by any of the means known in the art to be used for this purpose. Such means include gluing, crimping, heat sealing and ultrasonic bonding. One hot melt adhesive which works well is Eastobond A-3, marketed by the Eastman Chemical Products Company. The seam should be leak tight with respect to both the liquids and gases which do not pass back through the topsheet 26 from core means 30. This ensures that both are contained within the confines of the backsheet 28, except, of course, for any gases which are exposed to the deodorizing second lamina 12 and pass through the apertures 16 in the topsheet 26.

Once the catamenial pad 24 has been produced according to the manner described above, or any suitable manner, the pad 24 can be worn by the user. Any menstrual or other fluid discharge which is deposited on the outwardly oriented face of the first lamina 10, of topsheet 26, then passes through the laminate 14 in a first direction to the core means 30, where the liquids are collected. Any malodorous gases generated by the absorbed liquids are prevented from exiting the sides, ends, and bottom of the pad 24 by the impervious backsheet 28. As the malodors migrate towards the topsheet 26, the gases encounter, or are exposed to, the active of the second lamina 12.

The gases will be adsorbed, or otherwise acted upon, by the active of the second lamina 12 and present a diminished objectionable odor to the wearer. At the same time the cones 22 of the topsheet 26 provide vertical stanchions which keep the outwardly oriented face of the second lamina 12 above the elevation of the absorbed liquids, and generally dry. Only a small amount of malodorous gases, proportional to the topsheet 26 percent open area, will pass through the apertures 16.

A second execution of an exemplary catamenial pad 124 may be provided as shown in FIG. 6. A formed film apertured polyolefinic topsheet 126 is made according to any method well known in the prior art. An impervious backsheet 128 and absorbent core means 130 are also provided.

A modified form of the bicomponent laminate material is then constructed, resembling a flattened cylindrical tube 32, although a tube of any other shape is suitable. The tube 32 is constructed of a first lamina 10, such as the polyolefinic topsheet material, having outwardly positioned cones 22', which substantially prevent the entry of fluids, but not gases, into the tube 32 through apertures 16'. Inside the tube 32 is the second lamina 12 of activated charcoal, or other materials described above, which acts upon malodors. The charcoal 12 may be adhered to, or otherwise held by, a substrate 34 to prevent movement of the material of the second lamina 12 relative to the tube 32.

The tube 32 is then disposed in the catamenial pad 124, preferably in the axial direction. The tube 32 is disposed between the topsheet 126 and backsheet 128, preferably between the second face of the core means 130 and the underside of the topsheet 126. In a preferred second execution, the catamenial pad 124 comprises at least one, preferably two to four, such tubes 32 disposed substantially parallel to the sides of the catamenial pad 124. The tubes 32, provide good exposure of the second lamina 12 to the malodorous gases. If the second lamina 12 disposed within the tubes is activated charcoal, approximately 500 mg, equally divided between the tubes 32, is sufficient. The tubes 32, topsheet 126, backsheet 128, and core means 130 are registered, seamed and assembled as described above.

Similar to the action of the first execution, menses deposited on the topsheet 126 of the pad 124 are transmitted to the absorbent core means 130. The inside of the tubes 32 is not wetted by the menstrual liquids due to the repellant action of the outwardly oriented cones 22 on tubes 32. Gases generated by the absorbed liquids are collected in the pad 130 by the impervious backsheet 128. As the gases migrate towards the topsheet 126, the axial tubes 32 are encountered. The gases enter the tubes 32 and are exposed to the second lamina 12 contained therein. This substantially prevents such gases from exiting the pad 24 without exposure to odor control lamina 12 and being noticed by the wearer. Should tearing, or a breach, of the tube 32 occur, and liquids penetrate the tube 32, such liquids can be transmitted through the apertures 16' of the tube material to the core means 130.

Figure 8:
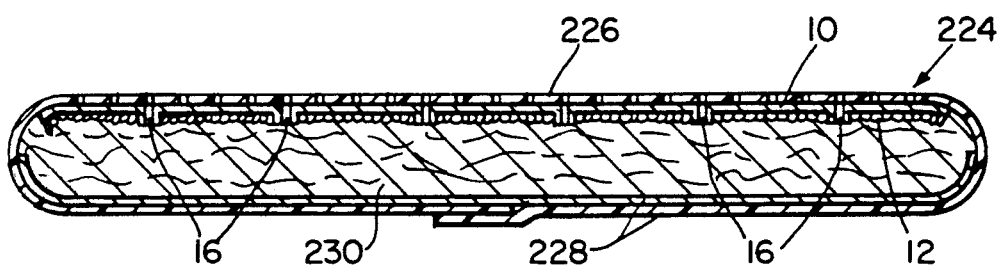
FIG. 8 is a cross-sectional view of a third embodiment of a catamenial pad of the type generally shown in FIG. 3, taken at a point corresponding to section line 4—4 of FIG. 3.

A third embodiment of a catamenial pad 224, illustrated in FIG. 8, shows the laminate 14 to be disposed between the topsheet 226 and backsheet 228. Preferably the laminate 14 is interposed between topsheet 226 and the second face of absorbent core means 230. This arrangement provides the advantage that the laminate 14 is more closely associated with core means 230. Any menses deposited on topsheet 226 will penetrate therethrough to the the outwardly oriented face of the first lamina 10 of laminate 14. Once the menses are deposited on the laminate 14, transmission through apertures 16 will occur and the menses will be retained by absorbent core means 230. Liquids in the core means 230 will be prevented from passing back through laminate 14 to the topsheet 226, and any malodorous gases which exit the core means 230 will be exposed to odor control lamina 12.

Obviously the laminate 14 of this invention could advantageously be placed at other locations of a catamenial pad. For example, the laminate 14 could be placed within the core means or near the backsheet and still act upon malodorous gases which develop within the catamenial pad and migrate towards second lamina 12.

If desired, a catamenial pad according to the first and third embodiments could be made to selectively incorporate the second lamina 12 al preferred locations. The topsheet 26 of the first embodiment and laminate 14 of the third embodiment could be constructed having first lamina 10 throughout, and second lamina 12 only near the center of the pad where the heaviest menstrual loading typically occurs. Alternatively, the density of the second lamina could be made to vary in accordance with the expected loadings and exposure to malodorous gases which will occur. For example, the second lamina 12 may be very heavily applied near the center of the pad, tapering to a less dense application near the edges of the pad. Other variations in the concentration of second lamina 12 should be utilized in accordance with the expected exposure to malodorous gases.

If will be apparent to one skilled in the art that the shape and size of either catamenial pad discussed above may be altered to yield a diaper, or adult incontinent product (not shown). Such an article has an absorbent core means disposed between a liquid impervious backsheet and a liquid pervious topsheet and is shaped to accommodate the waist and legs of the wearer. The diaper or adult incontinent product may be preformed to the shape of the wearer. A diaper constructed according to the teachings of U.S. Pat. No. 3,860,003 issued to Buell, which is incorporated herein by reference, works well.

The material of this invention may be advantageously incorporated into the diaper or incontinent pad as the topsheet. This arrangement provides the advantages that any urine or waste material which penetrates into the core means, and emits malodorous gases, will be retained by the core means and the resultant gases will be exposed to the odor control of the second lamina of the material of the topsheet.

The laminate of this invention may also be advantageously incorporated into bedding (not shown), particularly if a nonwoven material, which provides a cloth-like feel is selected for the first lamina. A laminate of suitable size is provided and placed over the bed with the first lamina upwardly oriented, towards the person who occupies the bed and the second lamina facing downwards. Any bodily fluids deposited on the bedding will be transmitted through the laminate and away from the skin of the person. Malodors generated by the transmitted fluids will be exposed to the second lamina and hence less noticeable. If desired, an absorbent pad may be placed beneath the laminate.

Various modifications may be made without departure from the spirit and scope of the invention. For example, several combinations of whiteners may be used in the first lamina of the laminate. It is also feasible to incorporate various active agents, including, but not limited to, those described above, in combination, into the second lamina. The catamenial pads described above may be combined to yield a catamenial pad having tubes and a bicomponent topsheet, or likewise a diaper or adult incontinent product having tubes and a bicomponent topsheet.

What is claimed is:

1. A bicomponent film laminate which transmits liquids deposited thereon in one direction and which exposes an active to malodors attempting to pass through said laminate in the opposite direction, said laminate comprising:
   (a) a first polymeric lamina exhibiting a pattern of discrete apertures therein, said first lamina having an exterior face and an interior face opposed thereto; and
   (b) a second active lamina comprising an odor control means, said second lamina having a first face adjacent said interior face of said polymeric lamina and a second face opposed thereto, said second lamina also exhibiting a pattern of discrete apertures substantially coinciding with said discrete apertures of said first lamina, whereby said laminate includes means for permitting liquids deposited on the exterior face of said first lamina to pass through said discrete apertures in said laminate without substantially wetting said second lamina, said laminate also including means for substantially preventing gaseous malodors from passing through said laminate in a direction opposite to the direction of liquid transmission without substantial exposure of the gaseous malodors to said second face of said second lamina.

2. A laminate according to claim 1 associated with a means for collecting liquids which pass through said laminate, said means being disposed adjacent the second face of said second lamina.

3. A laminate according to claim 1 associated with a means for collecting gases which are prevented from passing through said laminate in a direction opposite to that of said deposited liquids without substantial exposure of said gases to said second active lamina comprising an odor control means.

4. A laminate according to claim 1 wherein said first lamina and said second lamina are joined by means selected from the group consisting of adhesive bonding, mechanical entrapment and combinations thereof.

5. A laminate according to claim wherein said second lamina is applied to said first lamina by means selected from the group consisting of brushing, spraying and drawing said first lamina through a fluidized bed of said second lamina.

6. A laminate according to claim wherein said first lamina is selected from the group consisting of formed film and nonwoven materials.

7. A laminate according to claim 6 wherein said first lamina is selected from the group consisting of polyethylene, polyester, polypropylene, nylon, rayon, open cell foam and combinations thereof.

8. A laminate according to claim 6 or 7 further comprising from about 1 to about 15 weight percent of a whitener in said first lamina.

9. A laminate according to claim 6 wherein cones on said first lamina are oriented with their ends which are remote from the base plane of said first lamina pointed in the direction in which said liquids are transmitted to substantially prevent wetting of said second lamina.

10. A laminate according to claim 1 wherein said second lamina is selected from the group consisting of activated carbon, zeolites, molecular sieves, metal salts and combinations thereof.

11. A laminate according to claim 10 whereby said second lamina prevents malodors from passing through said laminate or said tube by means of adsorption, absorption, chemical reaction and combinations thereof 12. A laminate according to claim 10 or 11 wherein said second lamina imparts increased opacity to said laminate.

13. A laminate according to claim 11 wherein said second lamina is disposed at discrete sites of said laminate.

14. A laminate according to claim 11 wherein said second lamina varies in density.

15. A process for making a bicomponent laminate according to claim 1 comprising:
   (a) providing a first unapertured polyolefinic lamina;
   (b) providing a second active lamina material adapted to adsorb malodors;
   (c) applying said second lamina material to said first lamina in a thin uniform layer, thereby forming a unitary laminate; and
   (d) forming apertures through said laminate and cones surrounding said apertures simultaneously.

16. The process of claim 15 further comprising applying an adhesive intermediate said first unapertured lamina and said second lamina material.

17. The process of claim 15 further comprising heating said first lamina to its softening point and passing said first lamina and said second lamina material between pressure rolls, thereby embedding said second lamina material in said first lamina.

18. A disposable absorbent article for collecting liquids discharged from a source and substantially containing malodors generated by the collected liquids, said article comprising:
   (a) an absorbent core means for absorbing liquids, said core mean shaving a first face and a second face opposed thereto;
   (b) a liquid impermeable backsheet overlaying said first opposed face of said absorbent core means; and
   (c) a bicomponent film laminate topsheet overlaying said second opposed face of said core means and comprising a first polymeric lamina exhibiting a pattern of discrete apertures therein, said first lamina having an exterior face and an interior face opposed thereto; said laminate further comprising a second active lamina comprising an odor control means, said second lamina having a first face adjacent said interior face of said first lamina and a second face opposed thereto, said second face of said second lamina being directionally oriented toward said core means, said second lamina also exhibiting a pattern of discrete apertures substantially coinciding with said discrete apertures of said first lamina, whereby said laminate includes means for permitting liquids deposited on said exterior face of said first lamina to pass through said discrete apertures in said laminate to said core means without substantially wetting said second lamina said laminate also including means for substantially preventing gaseous malodors generated by the absorbed liquids from passing through said laminate in a direction opposite to the direction of transmission of deposited liquids without substantial exposure of the gaseous malodors to said second face of said second lamina.

19. A disposable absorbent article for collecting liquids discharged from a source and substantially containing malodors generated by the collected liquids, said article comprising:
- (a) an absorbent core means for absorbing liquids, said core means having a first face and a second face opposed thereto;
- (b) a liquid impermeable backsheet overlaying said first face of said absorbent core means;
- (c) a liquid permeable topsheet overlaying said second opposed face of said core means; and
- (d) at least one tube disposed between said backsheet and said topsheet, said tube having a first lamina comprised of polymeric film exhibiting a multiplicity of apertures, each circumscribed by an outwardly oriented cone adapted to resist the entry of liquids deposited thereon into said tube and to permit the entry of gaseous malodors into said tube, said tube further having a second lamina comprising an active agent located on its interior surface, said second lamina being adapted to substantially prevent gaseous malodors which enter said tube from exiting said tube without substantial exposure of the gaseous malodors to said active agent.

20. A disposable absorbent article for collecting liquids discharged from a source and substantially containing malodors generated by the collected liquids, said article comprising:
- (a) an absorbent core means for absorbing liquids, said core means having a first face and a second face opposed thereto;
- (b) a liquid impermeable backsheet overlaying said first opposed face of said core means;
- (c) a liquid permeable topsheet overlaying said second opposed face of said core means; and
- (d) a bicomponent film laminate disposed between said topsheet and said backsheet, said laminate comprising a first polymeric lamina exhibiting a pattern of discrete apertures therein, said first lamina having an exterior face and an interior face opposed thereto; said laminate further comprising a second active lamina comprising an odor control means, said second lamina having a first face adjacent said interior face of said first lamina and a second face opposed thereto, said second face of said second lamina being directionally oriented toward said core means, said second lamina also exhibiting a pattern of discrete apertures substantially coinciding with said discrete apertures of said first lamina, whereby said laminate includes means for permitting liquids deposited on said exterior face of said first lamina to pass through said discrete apertures in said laminate to said core means without substantially wetting said second lamina, said laminate also including means substantially preventing gaseous malodors generated by the absorbed liquids from passing through said laminate in a direction opposite to the direction of transmission of deposited liquids without substantial exposure of the gaseous malodors to said second face of said second lamina.

21. A disposable article according to claim 19 wherein said tube is disposed in axial direction relative to said disposable article.

22. A disposable article according to claim 21 having two to four substantially parallel tubes disposed in an axial direction.

23. A disposable article according to claim 21 wherein said tube is generally shaped like a flattened cylinder.

24. A disposable article according to claim 23 further comprising a substrate within said tube adapted to hold said second lamina and to substantially prevent movement of said second lamina relative to said tube.

25. A disposable article according to claim 15, 19 or 20 wherein said first lamina and and said second lamina are joined by means selected from the group consisting of adhesive bonding, mechanical entrapment and combinations thereof 26. A disposable article according to claim 15, 19 or 20 wherein said second lamina is applied to said first lamina by means selected from the group consisting of brushing, spraying and drawing said first lamina through a fluidized bed of said second lamina.

27. A disposable article according to claim 18, 19 or 20 wherein said first lamina is selected from the group consisting of formed film and nonwoven materials.

28. A disposable article according to claim 27 wherein said first lamina is selected from the group consisting of polyethylene, polyester, polypropylene, nylon, rayon, open cell foam and combinations thereof.

29. A disposable article according to claim 28 further comprising from about 1 to about 15 percent of a whitener disposed throughout said first lamina.

30. A disposable article according to claim 27 wherein cones on said first lamina are oriented with their ends which are remote from the base plane of said first lamina pointed in the direction in which said liquids are transmitted to substantially prevent wetting of said second lamina.

31. A disposable article according to claim 18, 19, or 20 wherein said second lamina is selected from the group consisting of activated carbon, zeolites, molecular sieves, metal salts and combinations thereof.

32. A disposable article according to claim 31 whereby said second lamina prevents malodors from passing through said laminate or said tube by means of adsorption, absorption, chemical reaction and combinations thereof 33. A disposable article according to claim 31 wherein said second lamina imparts increased opacity to said laminate.

34. A disposable article according to claim 31 comprising approximately 2.2 to approximately 8.8 mg activated charcoal per sq cm of second lamina.

35. A disposable article according to claim 32 wherein said second lamina comprises discrete sites of said active.

36. A disposable article according to claim 32 wherein said second lamina varies in density.

37. A disposable article according to claim 18, 19 or 20 further comprising an absorbent gelling material.

38. A disposable article according to claim 18, 19, or 20 further shaped to accommodate the legs and waist of the wearer, wherein said article is adapted for use as a diaper or adult incontinent product.

* * * * *

UNITED STATES PATENT AND TRADEMARK OFFICE
CERTIFICATE OF CORRECTION

PATENT NO. : 5,019,062

DATED : May 28, 1991

INVENTOR(S) : Leslie D. Ryan, Mark J. Steinhardt, Milton D. Spahni, James C. Baird It is certified that error appears in the above-identified patent and that said Letters Patent is hereby corrected as shown below:

Column 1, line 67, after "or" second occurrence, "first" should read -- interior --.

Column 2, line 14, "Specification" should read -- specification --.

Column 2, line 37, after "of" insert -- a --.

Column 3, line 29, after "London" insert a comma -- , --.

Column 4, line 64-65, delete "materials".

Column 7, line 36, "4" should read -- 14 --.

Column 8, line 8, after "been" insert -- found to work well and be sufficient to absorb a heavy menstrual --.

Column 8, line 13, "0" should read -- 30 --.

Column 9, line 64, delete "the", second occurrence.

Column 10, line 14, "al" should read -- at --.

Column 11, line 45, after "claim" insert -- 1 --.

Column 11, line 50, after "claim" insert -- 1 --.

Column 12, line 1, "whereby" should read -- wherein --.

Column 12, line 4, after "thereof" insert a period --.--.

Column 12, line 36, "mean shaving" should read -- means having --.

Column 14, line 11, "15" should read -- 18 --.

Column 14, line 12, delete "and" second occurrence.

UNITED STATES PATENT AND TRADEMARK OFFICE
CERTIFICATE OF CORRECTION

PATENT NO. : 5,019,062

DATED : May 28, 1991

INVENTOR(S) : Leslie D. Ryan, Mark J. Steinhardt, Milton D. Spahni, James C. Baird It is certified that error appears in the above-identified patent and that said Letters Patent is hereby corrected as shown below:

Column 14, line 16, "15" should read -- 18 --.

Column 14, line 45, after "thereof" insert a period -- . --.

Signed and Sealed this

Fifteenth Day of September, 1992

Attest:

DOUGLAS B. COMER

*Attesting Officer*  *Acting Commissioner of Patents and Trademarks*